United States Patent
Seiler et al.

(10) Patent No.: US 6,530,917 B1
(45) Date of Patent: Mar. 11, 2003

(54) DEVICE FOR PHOTOREFRACTIVE CORNEA SURGERY IN HIGHER-ORDER VISUAL DISORDERS

(75) Inventors: Theo Seiler, Zell (DE); Michael Mrochen, Dresden (DE); Maik Kaemmerer, Dresden (DE)

(73) Assignee: Wavelight Laser Technologie AG, Erlangen (DE)

( * ) Notice: Subject to any disclaimer, the term of this patent is extended or adjusted under 35 U.S.C. 154(b) by 0 days.

(21) Appl. No.: 09/647,439

(22) PCT Filed: Feb. 2, 2000

(86) PCT No.: PCT/EP00/00827

§ 371 (c)(1),
(2), (4) Date: Sep. 28, 2000

(87) PCT Pub. No.: WO00/45759

PCT Pub. Date: Aug. 10, 2000

(30) Foreign Application Priority Data

Feb. 5, 1999 (DE) .......................... 199 04 753

(51) Int. Cl.$^7$ .............................................. A61B 18/20
(52) U.S. Cl. ............................................. 606/5; 606/4
(58) Field of Search ........................................ 606/4–5

(56) References Cited

U.S. PATENT DOCUMENTS

| | | | |
|---|---|---|---|
| 5,258,791 A | | 11/1993 | Penney et al. |
| 5,949,521 A | * | 9/1999 | Williams et al. ............. 351/246 |
| 6,050,687 A | * | 4/2000 | Bille et al. .................... 351/212 |
| 6,075,650 A | * | 6/2000 | Morris et al. ................ 359/641 |
| 6,095,651 A | * | 8/2000 | Williams et al. ............. 351/246 |
| 6,199,986 B1 | * | 3/2001 | Williams et al. ............. 351/221 |
| 6,270,221 B1 | * | 8/2001 | Liang et al. ................. 351/221 |
| 6,271,915 B1 | * | 8/2001 | Frey et al. ................... 356/124 |

FOREIGN PATENT DOCUMENTS

| | | |
|---|---|---|
| WO | WO 95/28989 | 11/1995 |
| WO | WO 98/27863 | 7/1998 |
| WO | WO 99/27334 | 6/1999 |

OTHER PUBLICATIONS

H. C. Howland et al., Journal of the Optical Society of America, 67(11): 1508–1518, Nov., 1977.
G. Walsh et al., Optical Society of America, vol 1, No. 9, 987–992, Sep., 1984.
G. Walsh et al., Ophthal. Physiol. Opt., vol. 5, 23–31, 1985.
T. Seiler et al., Laser and Light in Ophthamology, vol. 5, No. 4, 199–203, 1993.
J. Liang et al., Optical Society of America, 11(7): 1949–1957, Jul., 1994.
G. Smith et al., Ophthal. Physiol. Opt., vol. 16, No. 3, 222–229, 1996.

(List continued on next page.)

*Primary Examiner*—Lee Cohen
*Assistant Examiner*—Henry M. Johnson, III
(74) *Attorney, Agent, or Firm*—Clifford W. Browning; Woodard, Emhardt, Naughton, Moriarty & McNett LLP

(57) ABSTRACT

A device for photorefractive cornea surgery, in particular LASIK and PRK, of the eye for the correction of sight defects of a higher order provides for the following devices:

an aberroscope (12, 14, 16, 22, 24, 28) for measuring the wave-front aberration of the entire optical system of the eye to be corrected in relation to a specific eye position, means (48) for deriving a photoablation profile from the measured wave-front aberration in such a way that a photoablation in accordance with the photoablation profile minimises the wave-front aberration, and a laser radiation source (30) and means (32, 38, 40, 48) for controlling the laser radiation in relation to the specific eye position in accordance with the photoablation profile.

6 Claims, 3 Drawing Sheets

OTHER PUBLICATIONS

K.M. Oliver et al., Journal of Refractive Surgery, vol. 13, 246–254, May/Jun., 1997.

J.K. Shimmick et al., Journal of Refractive Surgery, vol. 13, 235–245, May/Jun., 1997.

J. Liang et al., Journal of the Optical Society of America, vol. 14, No. 11, 2873–2883, Nov., 1997.

C.E. Martinez et al., Arch. Ophthalmol., vol. 116, 1053–1062, Aug., 1998.

N. Lopez–Gil, Journal of the Optical Society of America, vol. 15, No. 9, 2563–2571, Sep., 1998.

G.F. Marshall, Laser Focus World, Jun., 1994, p. 57.

* cited by examiner

DEVICE FOR PHOTOREFRACTIVE CORNEA SURGERY IN HIGHER-ORDER VISUAL DISORDERS

The invention relates to a device for photorefractive surgery on the cornea of the eye for the correction of sight defects of a higher order.

Photorefractive keratectomy is a hitherto widely established procedure for correcting defective vision of a lower order, i.e. for example of myopia, hyperopia, astigmatism, myopic astigmatism and hyperopic astigmatism. The term "photorefractive keratectomy (PRK)" is usually understood to mean that an intervention on the surface of the cornea is only intended after the so-called corneal epithelium has been removed. After removal of the epithelium the Bowman's membrane or the corneal stroma is exposed and can be removed by a laser. The LASIK procedure (laser in situ keratomileusis) is generally distinguished from PRK. In the LASIK procedure an approximately 100 $\mu$m to 200 $\mu$m thick cornea slice (so-called "flap") with a diameter of 8 to 10 mm is cut down to a small remnant serving as a "hinge" with a so-called microkeratome. This slice (flap) is folded to the side and ablation (removal) of material is then effected by laser radiation directly in the stroma, i.e. not on the surface of the cornea. After laser treatment the lid is folded back to its original position again and healing generally takes place relatively quickly.

The invention described below is suitable both for the above-described PRK as well as in particular the LASIK technique.

In PRK and in LASIK, corneal material is removed. The removal is a function of the lumination of the laser beam striking the cornea (energy per unit of area). Various techniques are known for beam formation and beam positioning thus, for example, the so-called slit scanning, in which the radiation is guided by means of a moved slit over the region to be treated, the so-called scanning-spot, in which a radiation spot with very small dimensions is guided over the area to be removed, and also the so-called full-ablation or widefield ablation, in which the radiation is directed extensively over the entire area to be removed and wherein the lumination alters across the beam profile in order to achieve the desired removal of cornea. The state of the art includes suitable algorithms for controlling the radiation for the aforementioned beam positioning in each case in order to remove the cornea such that the cornea finally has the desired radius of curvature.

The aforementioned scanning-spot uses a laser beam focused on a relatively small diameter (0.1 to 2 mm), which laser beam is directed by means of a beam positioning device onto various points of the cornea and is moved successively by a so-called scanner such that ultimately the desired removal of cornea is achieved. Removal takes place therefore in accordance with a so-called ablation profile. In PRK and LASIK so-called galvanometric scanners can in particular be used (cf. Essay by G.F. Marshall in LASER FOCUS WORLD, June 1994, page 57). In the meantime other scanning techniques have been disclosed for the positioning of the laser beam.

According to the state of the art, the aforementioned types of defective vision of a lower order (for example myopia, hyperopia, astigmatism) are at present determined according to the so-called refraction data of the patient's eye i.e. the dioptric value measured for the patient's eye determines the ablation profile in accordance with which material is removed (ablated) from the cornea (cf. T. Seiler and J. Wollensak in LASERS AND LIGHT IN OPHTHALMOLOGY, Vol. 5, No. 4, pages 199 to 203, 1993). In accordance with this state of the art, for a given patient's eye with a specific dioptric value the laser radiation is therefore guided over the cornea such that a predetermined ablation profile corresponding, for example, to a parabola in a correction for myopia is removed. In other words: the ablation profile is adapted only in accordance with the dioptric value to the individual eye but not however in accordance with local irregularities of the optical system "eye".

The essay by J. K. Shimmick, W. B. Telfair et al in JOURNAL OF REFRACTIVE SURGERY, Vol. 13, May/June 1997, pages 235 to 245 also describes the correction of sight defects of a lower order by means of photorefractive keratectomy, wherein the photoablation profiles correspond to theoretical parabolic shapes. Furthermore, it is only proposed there to incorporate some empirical correction factors into the ablation profile, which correction factors take into account the interaction between laser and tissue in order to achieve a paraboloid-shaped removal on the eye as a result.

A particular problem in photorefractive kerotectomy and LASIK is the relative positioning of laser beam and eye. The state of the art knows various processes for this thus, for example, so-called "eye trackers", i.e. devices which determine the movements of the eye in order to then control (track) the laser beam used for the ablation in accordance with the eye movements. DE 197 02 335 C1 for example, describes the state of the art with regard to this.

As aforementioned above, the procedures for photorefractive cornea surgery of the state of the art for correcting defective vision of a lower order are substantially "all-inclusive procedures" in the sense that the correction takes account of the (all-inclusive) dioptric value of the eye. Such defective vision of a low order can, for example, be corrected with spherical or astigmatic lenses or also with a photorefractive correction of the cornea.

The optical image in the eye is however affected not only by the aforementioned types of defective vision of a lower order but also by so-called image distortions of a higher order. Such image distortions of a higher order occur in particular after operative interventions to the cornea and inside the eye (cataract operations). Such optical aberrations can be the reason why complete visual acuity (visus) is not attained despite a medical correction of a defect of a lower order. In DER OPHTHALMOLOGE, No. 6, 1997, page 441 P. Mierdel, H.-E. Krinke, W. Wigand, M. Kaemmerer and T. Seiler describe a measuring arrangement for determining the aberration of human eyes. With such a measuring arrangement, aberrations (image distortions) for monochromatic light can be measured, more specifically aberrations caused by the cornea as well as image distortions caused by the entire ocular image system of the eye can be measured and this can be done site-dependently, i.e. with a specific resolution for given sites within the pupil of the eye, it can be determined how large the image distortion of the entire optical system of the eye to be corrected is at this point. Such image distortions of the eye are mathematically described in the above-aforementioned work by P. Mierdel et al as a so-called wave-front aberration. Wave-front aberration is understood to mean the spatial course of the distance between the actual light wave-front of a central light point and a reference surface, such as, for example, its ideal, ball-shaped form. Therefore, the ball surface of the ideal wave-front, for example, serves as a spatial reference system. It is also known as such in the state of the art to select a plane as a reference system for the aberration measurement if the ideal wave-front to be measured is flat.

The measuring principle according to the aforementioned work by P. Mierdel, T. Seiler et al is also used as a starting point in the realisation of the present invention. It substantially involves a parallel beam bundle of sufficient diameter being divided by a shadow mask into separated parallel individual beams. These individual beams pass through a convex lens (so-called aberroscope lens) and as a result are focused in the emmetropic eye at a specific distance in front of the retina. The result is clearly visible projections of the mask shadows on the retina. This retinal light point pattern is depicted according to the principle of indirect ophthalmoscopy onto the sensor surface of a CCD video camera. In the aberration-free ideal eye the depicted light point pattern is not distorted and corresponds to the shadow mask pattern exactly. If there is an aberration however, there are individual displacements of each pattern point because each individual beam passes through a specific cornea or pupil region and in accordance with the irregular optical effect experiences a deviation from the ideal course. Finally the wave-front aberration is determined by a method of approximation as a site function over the pupil surface from the displacements of the retinal pattern points. The aforementioned state of the art also describes the mathematical representation of this wave-front aberration in the form of a so-called "wave-front aberration mountain range". This "wave-front aberration mountain range" gives a value for the wave-front aberration $W(x, y)$ over each pupil site (x-y coordinates), which value is then plotted as a value over the x-y coordinates. The higher the "mountain range" the larger the image distortions in the eye at the respective pupil site. In a first approximation there is a proportionality between the measured deviation of the corresponding retinal light point from its ideal position and the steepness of the "wave-front aberration mountain range" for each incident light beam. Thus as a result the wave-front aberration can be determined as a site function based on an arbitrary reference value on the optical axis of the system. Ideal, generally undistorted light point positions on the retina, which can supply the reference value are, for example, four central points with little mutual spacing. Such points represent a central cornea/pupil zone of approximately 1 to 2 mm diameter which, in accordance with experience, can be accepted as being generally free of image distortions of a higher order.

The "wave-front aberration mountain range" can be illustrated in various ways mathematically with the aid of a closed expression (a function). Approximations in the form of a sum of Taylor or also in particular Zernike polynomials are considered in particular. The Zernike polynomials have the advantage that their coefficients are directly related to the generally known image distortions (opening defects, coma, astigmatism, distortion). The Zernike polynomials are a set of completely orthogonal functions. In an essay by J. Liang, B. Grimm, S. Goelz and J. F. Bille, "Objective measurement of wave aberrations of the human eye with the use of a Hartmann-Shack wave-front sensor", Optical Society of America, 11(7):1949–1957, July 1994, it is shown how the wave-front (or wave-front aberration) can be calculated from the grid point displacements. The actual wave-front can be ascertained from the determining of the derivation function of the wave-front. The wave-front emerges as a solution to an equation system. The essay by H. C. Howland and B. Howland, "A subjective method for the measurement of monochromatic aberrations of the eye", Journal of the Optical Society of America, 67(11):1508–1518, November 1977, also describes a procedure for determining the monochromatic aberration and the ascertaining of the first fifteen Taylor coefficients. This state of the art can be consulted.

A measurement of the aberration and the retinal image quality of the human eye is also described in the following essay: "Aberrations and retinal image quality of the normal human eye", Junzhong Liang and David R. Williams, Journal Optical Society America A, Vol. 14, No. 11, November 1997, pages 2873 to 2883.

In WO 99/27334 (published after the priority date of the present application) the wave-front aberration of the eye is measured and used for the subsequent ablation.

The state of the art also already knows the attempt to ascertain ablation profiles (removal profiles) individually and site dependently for an eye to be corrected and this is based on so-called topographical measurements of the surface of the cornea, cf. C. E. Martinez, R. A. Applegate et al in ARCH OPHTHALMOL/Vol. 116, August 1998, pages 1053 to 1062. Such topographies of the surface of the cornea only supply data however on the cornea curvature, i.e.. height data at each point of the surface of the cornea. Whilst aberrations can be calculated from this data, this data does however only supply defects of a higher order on the surface of the cornea and not aberration values for the entire optical system "eye". The resolution capacity of the eye (visus) is determined however not only by the surface of the cornea but also by the entire optical system of the eye to be corrected (for example the eye lens also), so an improvement is also desirable in this context.

The object of the invention, starting from this state of the art, is to provide a device for photorefractive keratectomy with which sight defects of a higher order can be treated.

For the solution of this technical problem the invention provides a combination comprising the following devices:

an aberroscope for measuring the wave-front aberration of the entire optical system of the eye to be corrected in relation to a specific eye position, means for deriving a photoablation profile from the measured wave-front aberration in such a way that a photoablation in accordance with the photoablation profile minimises the wave-front aberration of the treated eye, and a laser radiation source and means for controlling the laser radiation in relation to the specific eye position for the removal of the photoablation profile.

A preferred design of the device according to the invention is characterised by a device for determining an instantaneous eye position and a device for adapting the photoablation profile to the eye position.

The device according to the invention therefore serves in particular to carry out a procedure for the photorefractive keratectomy of the eye to correct sight defects of a higher order with at least the following steps:

aberroscopic measuring of the wave-front aberration of the entire optical system of the eye to be corrected in relation to a specific eye position, deriving a photoablation profile from the measured wave-front aberration to minimise the wave-front aberration, and photoablation by laser radiation in accordance with the photoablation profile in relation to the specific eye position.

A further procedure for the photorefractive keratectomy of the eye to correct sight defects of a higher order can also be carried out. With this procedure or with a device carrying out this procedure, both of which will be described in more detail below, the ablation profile is calculated directly from the projection of points onto the cornea and the retina. "Projection" here means that a light beam of small diameter is directed onto the cornea, produces the aforementioned point there and passes from the cornea to the retina where it produces a further point. The points are light spots. A change in the curvature of the surface of the cornea can be inferred from a deviation of the position of the light spot on the retina from a desired position (the desired position corresponds to an aberration-free eye) (see below) and this ultimately represents a statement about the derivation function (in the mathematical sense) of the sought ablation profile. If this procedure is carried out with a sufficient number of light beams which are directed at different points of the eye, the derivation function of the ablation profile can be ascertained over the entire surface of the eye concerned and the ablation profile itself can then be calculated mathematically therefrom. The invention also involves the apparatus for carrying out this procedure, i.e. in particular the means for directing selected light beams with defined positions and angles of incidence, the means for measuring a displacement of the light beam on the retina in relation to the desired position and the correspondingly programmed computer for ascertaining photoablation profiles from these measurements of light beam positions on the retina.

An embodiment of the invention will be described in more detail below with the aid of the drawings, in which:

FIG. 1 shows schematically the wave-front aberration of an eye already explained above, i.e. the deviation of the actual, aspherical wave-front from the ideal wave-front. A is the optical axis of the system and F the focal point, the latter is also the imaginary starting point of the radiation in the case of an ideal wave-front.

Figure 1:
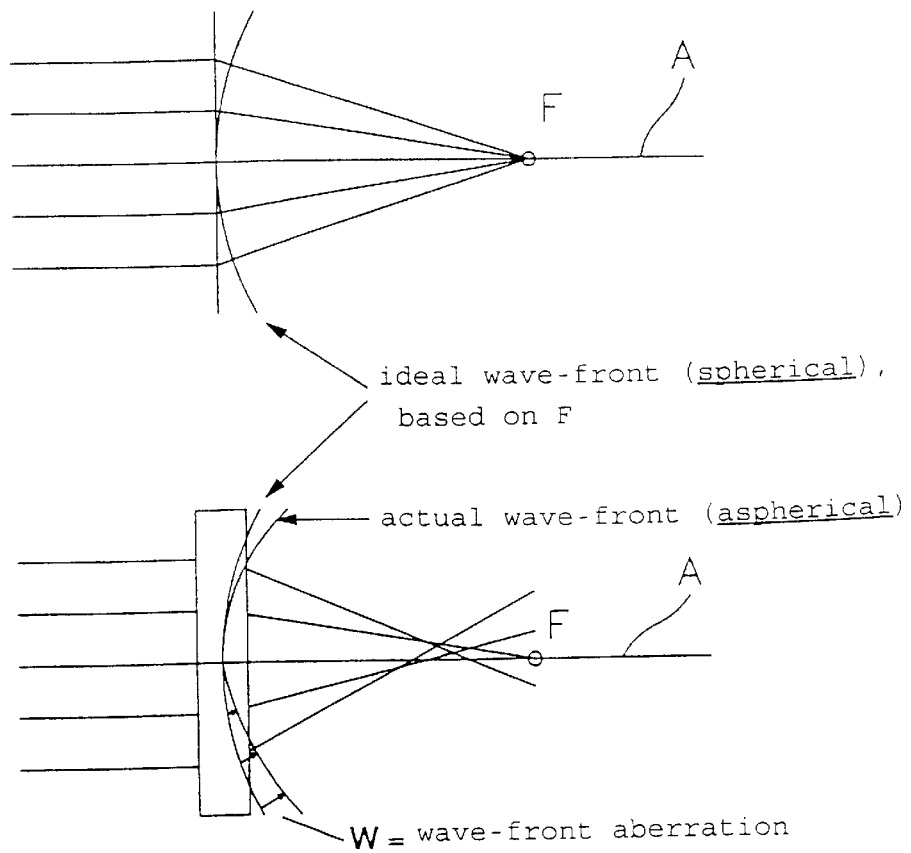
FIG. 1 shows schematically the wave-front aberration.
Figure 2:
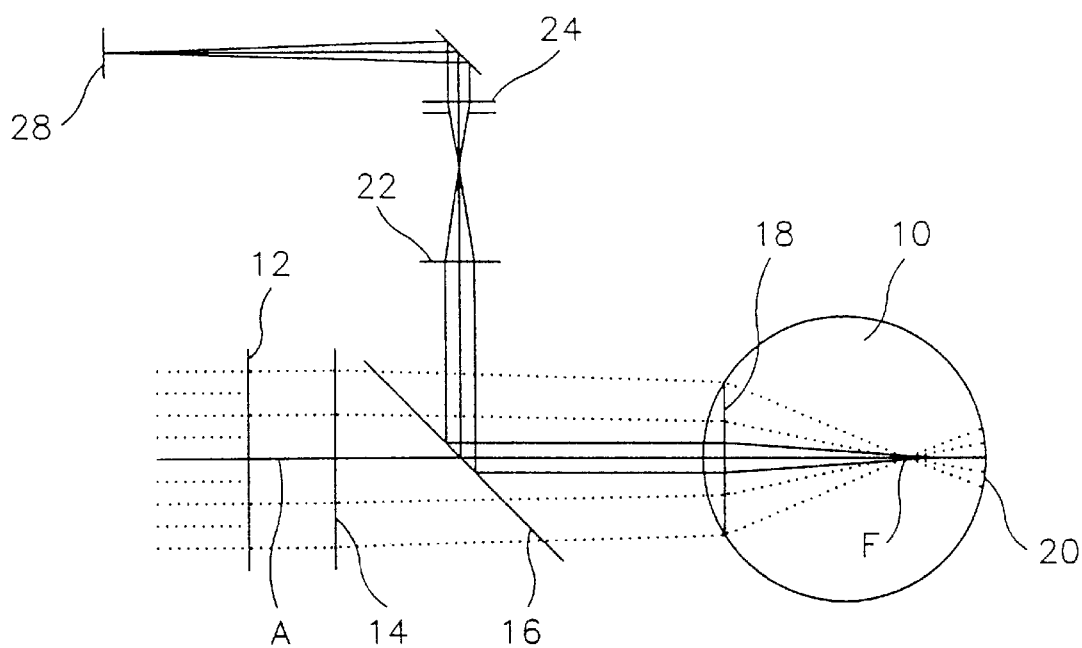
FIG. 2 shows schematically an aberroscope for measuring the wave-front aberration of the entire optical system of an eye to be treated.

FIG. 2 shows schematically the optical diagram of a video aberroscope for measuring the wave-front aberration of an eye 10. The green light of an HeNe laser (543 nm) is widened to a diameter of approximately 12 mm and subsequently divided by means of a shadow mask 12, in which a large number of equidistant apertures are formed, into a corresponding number of parallel individual beams. In accordance with FIG. 2 these individual beams, which are only shown schematically by dotted lines, extend parallel to the optical axis A of the system. Using an aberroscope lens 14 (convex lens) in front of the eye 10 these beams are refracted such that they are focused at a specific distance in front of the retina 20 (focus F). In a right-sighted eye the aberroscope lens has a lens power of +4 dpt for example. In the aberration-free ideal eye, a completely undistorted light point pattern is formed in this manner on the retina 20. The pupil is indicated by the reference numeral 18.

If the eye 10 does have an aberration however, the pattern points are displaced in accordance with the image distortions as each individual beam passes only one quite specific site of the pupil 18 and, in accordance with the irregular optical effects, experiences a deviation from the ideal course. This deviation from the ideal course corresponds to the optical image distortion of the entire optical system of the eye 10 with regard to a light beam which passes the specific site inside the pupil. On the cornea the individual beams, for example, in x- and y-direction have a constant spacing of 1.0 mm and their diameter is, for example, approximately 0.5 mm. The entire parallel measuring beam bundle has, for example, a dimension of 8×8 mm on the cornea.

The light point pattern produced on the retina 20 is depicted by means of a half mirror 16 via an ophthalmoscope lens 22 and an objective 24 for the retinal image onto a sensor surface 28 of a solid-state image camera (CCD camera) in order to process the resulting light point pattern for calculation. The deviations of the sites of the light points based on the equidistant, regular structure of the defect-free eye result in the possibility of ascertaining the wave-front aberration W (x, y) as a site function over the pupil surface of the eye. The site function can be approximated by means of a set of polynomials, for example Taylor polynomials or Zernike polynomials. The Zernike polynomials are preferred here because their coefficients $C_i$ have the advantage of a direct relationship with the image distortions such as opening defects, coma, astigmatism, distortion. The wave-front aberration W can be represented by the Zernike polynomials $Z_i$ (x, y) as follows:

$$W(x, y) = \Sigma_i C_i \times Z_i(x, y).$$

The Cartesian coordinates in the pupil plane are designated by (x, y).

The determining of, for example, the first fourteen coefficients $C_i$ (i=1, 2, . . . , 14) of the Zernike polynomials allows a sufficiently exact description of the wave-front aberration W (x, y) as a function of the site coordinates of the free pupil surface. A so-called wave-front aberration mountain range is thus produced, i.e. in a three-dimensional representation a function over the site coordinates x, y which gives the local image distortions in each case. Other possibilities can also be selected in addition to the Zernike polynomials to mathematically describe the wave-front, for example Taylor's series. The Zernike polynomials are merely the embodiment selected here.

Figure 3:
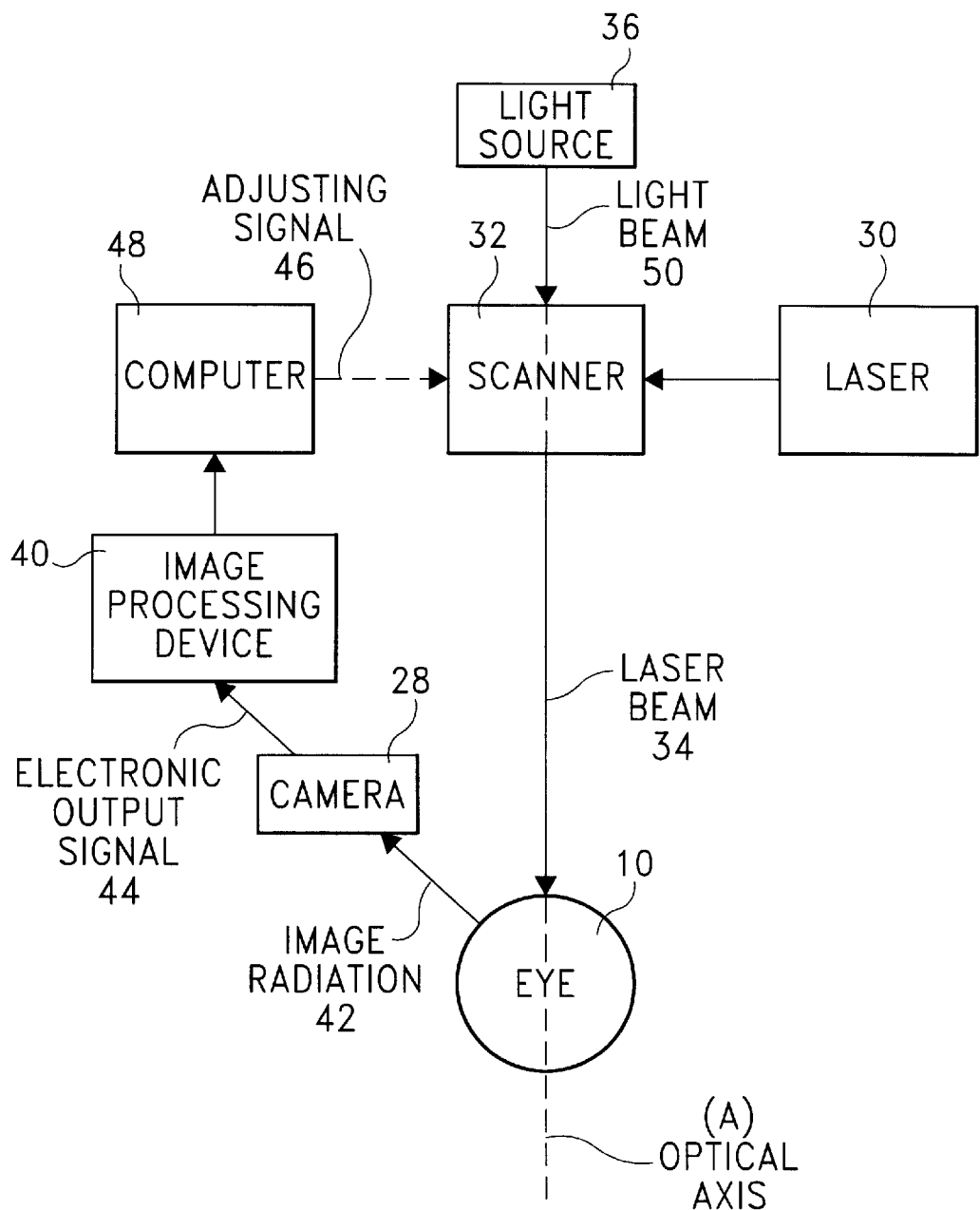
FIG. 3 shows schematically a measuring and control arrangement for carrying out a photorefractive keratectomy of the eye, means for deriving a photoablation profile and means for controlling the laser radiation.

A so-called photoablation profile is calculated from this wave-front aberration W (x, y) by means of a computer 48 (FIG. 3). Ultimately, the computer therefore ascertains from the light point pattern the wave-front aberration in the form of a specific number of Zernicke coefficients and then from the wave-front aberration a photoablation profile, i.e. data on the depth to which the cornea must be removed (ablated) at the respective pupil site in order to reduce the wave-front aberration. The ablation profile, i.e. the layer thickness of the material to be removed as a function of the site (X-Y coordinates) can be determined in various different ways from the wave-front (aberration): the ablation profile for an eye to be corrected is fundamentally calculated with a corresponding eye model.

To this end the wave-front aberration on the surface of the cornea is mathematically projected taking into account the geometric properties of the eye, such as, for example, the cornea thickness, distance between cornea posterior surface and lens anterior surface, distance between lens anterior surface and lens posterior surface, distance between lens posterior surface and retina. Furthermore, the refractive indexes of the individual optical elements of the eye are taken into account (for example tear film n=1.337, cornea n=1.37, aqueous humour n=1.337 etc.) in the calculation of the ablation profile. The wave-front substantially describes the running time differences of the light, i.e. the optical paths. If the optical paths are divided by the refractive index, the geometric path is obtained. Thus the relevant ablation profile can be derived from the projection of the wave-front onto the cornea. At the given point of the cornea an ablation depth (with LASIK corresponding to a depth of the material ablated in the stroma) it is mathematically assumed and calculated in the form of an iteration how such an ablation would affect the running time differences of the beams. The aim is to adapt the running times of the beams at all sites of the cornea in such a way that the wave-front aberration is as low as possible. In doing so it must also be taken into account that the wave-front can also have values which in their physical significance indicate a layer of tissue (i.e. a thickening of the cornea) which is generally not possible. As a result the ablation profile must be adapted accordingly, i.e. displaced as a whole such that the desired finished profile of the cornea is only achieved by ablation (removal) of tissue.

The wave-front aberration can be calculated not only in the pupil plane (entrance pupil) but also directly on the cornea. Therefore, taking into account the corresponding refractive indexes the actual ablation profile results for a specific pupil diameter.

A particular aspect of the invention is that a correction of the wave-front aberration W (x, y) used for ascertaining the ablation profile is undertaken such that the healing process of the eye after the operation is also taken into account. It has in fact emerged that a change in the optical properties of the eye results from the healing process and that in order to achieve the best results these changes should be taken into account in the wave-front aberration used as a basis. This is carried out as follows:

So-called correction factors ("fudge factors") are introduced into the above equation in which the wave-front aberration W (x, y) is represented as a sum of Zernike polynomials $Z_i$ (x, y):

$$W(x, y) = \sum_{i=0}^{n} A_i \times C_i \times Z_i(x, y)$$

In comparison with the above formula, correction factors $A_i$ have been added to the sum of Zernicke coefficients and Zernike polynomials in each case, which correction factors empirically take into account the wound healing process. In other words: the present function W (x, y) describes the wave-front on the eye to be corrected taking into account post-operative changes of individual optical image distortions ($Z_i$) by the healing of the wound. In this case the Zernicke coefficients of the zero to eighth order are particularly clinically relevant. The polynomial coefficients $C_i$ describe, as already explained above, the magnitude of the image distortion from the described measurement.

It has been empirically found that the clinically relevant value range of correction factors Ai is in the region of −1000 to 0 to +1000. It has also been empirically ascertained that the clinical correction factors $A_i$, assume different values for each coefficient $C_i$. $A_i$ is therefore a function of $C_i$. This functional dependence $A_i=f_i$ ($C_i$) is different for the individual coefficients $C_i$, i.e. the function $f_i$ has different courses for the individual coefficients $C_i$.

It has furthermore been found that the function $a_i=f_i$ ($C_i$) is furthermore dependent on the therapeutic laser system used in each case as the post-operative healing process is itself dependent on the laser system used in each case. This means that as a rule no generally valid (abstract) data can be given for the clinical correction factors $A_i$, rather these correction factors have to be empirically (experimentally) ascertained clinically for the laser system used in each case, wherein the above-aforementioned typical value range of −1000 via 0 to +1000 applies, in particular to the laser system used here, with the commercial name "Allegretto" from the company Wave-Light, Erlangen, Germany.

As stated, when the above-aforementioned correction factors $A_i$ are not used this can lead to a overvaluation or undervaluation of individual image distortions as a result of the healing of the wound after the refractive intervention, in the case of LASIK therefore inter alia the healing of the folded back slice ("flap"), on the basis of the ablation profile ascertained from the wave-front aberration. For the correction of a coma, for example, of approximately $Z_7$=0.3 $\mu$m, a coma $Z_7$=0.5 $\mu$m has to be removed from the cornea in order that after the wound has fully healed (for example, closure of the epithelium, approximately 7 days) a $Z_7$=0 results ("Z" here stands for the Zernicke coefficients as an example).

The correction factors $A_i$ ascertained in accordance with the above guidelines are stored in the computer and the computer programme incorporates them (automatically) into the ablation profile ultimately used.

As an alternative to the above-described calculation of the ablation profile from the wave-front aberration, the ablation profile can also be calculated directly from a projection of points onto the cornea and the retina. If a light beam with known angles of incidence and coordinate points falls onto the cornea and then into the eye, this light beam is depicted on the retina in accordance with the optical properties of the eye. As the position of the light beam on the cornea and the angle of incidence of the beam are known, the optical beam path can be reproduced by measurement of the position of the light beam on the retina. If in doing so it is established that the position of the light beam on the retina deviates from the desired position (the desired position means an aberration-free image), the aberration can be ascertained from the position deviation. The light is refracted according to the geometric curvature of the surface of the cornea and the further aberration defects of the "eye" system. The above-mentioned position deviation of the light beam on the retina can be expressed by a corresponding change in the angle of incidence. The angle of incidence is proportional to the derivation function of the surface of the cornea. By proceeding iteratively a (pathological) change in the curvature of the surface of the cornea can be inferred from the position displacement of the light beam on the retina and the change in the angle of incidence connected therewith. The change in the curvature of the surface of the cornea therefore describes the derivation function of the (sought) ablation profile. If this procedure is carried out with a sufficient number of light beams at different points of the eye (for example by projection of a grid onto the cornea), the entire derivation function of the (sought) ablation profile can be determined. As a result the ablation profile can be calculated by known mathematical processes (for example spline interpolation and subsequent integration).

It has been found that ablation profiles which have been obtained by wave-front measurements in some instances necessitate a so-called transition zone because without such a transition zone a certain amount of residual material would possibly remain at the edge of the ablation profile, i.e. a step would be produced on the cornea. In order to avoid such steps, a transfer zone approximately 0.5 mm to 3 mm wide is provided around the ablation profile in order to ensure a smooth, step-less surface over the entire cornea.

FIG. 3 shows schematically the computer and control system for carrying out photoablation in accordance with the calculated photoablation profile. Photoablation takes place both superficially on the cornea and intra-stromally.

An excimer laser (193 nm) is considered in particular as a laser 30 for the photablation. Er:YAG solid-state lasers with a wavelength of 2.94 $\mu$m and UV solid-state lasers (for example Nd:YAG with 213 nm) are also considered in particular.

The laser radiation is deflected by means of a galvanometric scanner 32 and the deflected laser beam 34 is directed onto the eye 10.

A further beam of a so-called positioning light source 36 is directed coaxially to the laser beam 34 onto the eye 10. The beam 50 of the positioning light source 36 defines a reference axis A which is spatially fixed.

In reality the eye 10 moves in relation to the axis A. In order to adapt (track) the processing beam 34 and accordingly the ablation profile to be removed to the movements of the eye during such movements, the eye is illuminated with infrared radiation (not shown) and images are taken with a specific image sequence frequency by means of the CCD camera 28. The image radiation 42 of the eye therefore produces images in the CCD camera 28 which are electronically processed. The electronic output signal 44 of the camera 28 is supplied to a image processing device 40 and the result of the image processing is input into a computer 48 which carries out both the evaluation and the control of the scanner 32. The image processing and the positioning of the eye and the adaptation of the scanner movement and thus of the ablation profile to the instantaneous position of the eye are known as such (DE 197 02 335 C1). The computer 48 therefore emits a corresponding adjusting signal 46 to the scanner 32 so the laser beam 34 is controlled such that in relation to a specific eye position, in relation to which the wave-front ablation has also been measured, the ablation profile is also removed. In this way the optical defects of the entire eye can be corrected by photoablation of the cornea. The ablation profile removed here in the present context is the ablation profile obtained from the wave-front measurement and altered by the above-described empirical correction factors on the basis of the healing of the wound.

In the embodiment dealt with above the wave-front aberration was ascertained by means of grid point displacement (for example in accordance with the work by J. Liang et al). In principle it is possible to measure the wave-front aberration in other ways (for example in accordance with the above-aforementioned work by H. C. Howland and B. Howland) or also in accordance with a work by G. Smith, R. A. Applegate and H. C. Howland, Ophthal. Physiol. Opt. Vol. 16, No. 3, pages 222 to 229, 1996 or the work by G. Walsh, W. N. Charman and H. C. Howland in Optical Society of America 1984, pages 987 to 992.

What is claimed is:

1. Device for photorefractive surgery on a cornea of an eye for the correction of sight defects of a higher order, said device comprising:

an aberroscope (12, 14, 16, 22, 24, 28) for measuring the wave-front aberration of the entire optical system of the eye to be corrected in relation to a specific eye position, means (48) for deriving a photoablation profile from the measured wave-front aberration in such a way that a photoablation in accordance with the photoablation profile minimizes the wave-front aberration of the treated eye, and a laser radiation source (30) and means (32, 28, 40, 48) for controlling the laser radiation in relation to the specific eye position in accordance with the photoablation profile, wherein
the means (48) for deriving a photoablation profile by means of the measured wave-front aberration contain stored correction factors, in accordance with which the photoablation profile derived by means of the measured wave-front aberration is changed.

2. Device for photorefractive surgery on a cornea of an eye for the correction of sight defects of a higher order, said device comprising:

means for directing a plurality of light beams with defined angles of incidence at defined points onto the cornea and the retina of the eye, means for determining a possible deviation of an actual position of a light beam on the retina from a desired position which corresponds to an aberration-free eye, means for determining a derivation function of a sought photoablation profile from the determined deviations of the actual positions from the desired positions for the individual light beams, means for calculating a photoablation profile by means of the derivation function, and a laser radiation source (30) and means (32, 28, 40, 48) for controlling the laser radiation in relation to a specific eye position in accordance with the photoablation profile, wherein
the number of light beams directed onto the cornea and the retina of the eye is sufficient to determine the derivation function over the entire surface of the eye concerned.

3. Device according to claim 2, wherein
the means for directing a plurality of light beams onto the cornea and the retina of the eye project a light point pattern onto the cornea.

4. Device according to claim 2, characterised in that the means (48) for calculating a photoablation profile by means of the derivation function have stored correction factors in order to correct the photoablation profile calculated by means of the derivation function.

5. Device according to one of claims 1 or 4, wherein the stored correction factors correspond to a change in the refractive properties of the cornea as a result of a postoperative healing process.

6. Device according to one of claims 1 or 4, wherein the correction factors enter into an ascertained wave-front aberration W (x, y) as follows:

$$W(x, y) = \sum_{i=0}^{n} A_i \times C_i \times Z_i(x, y),$$

wherein $Z_i$ are the Zernicke polynomials, $C_i$ are the polynomial coefficients, $A_i$ are the correction factors, i is a running index from 0 to n and n is the number of Zernicke polynomials which are used.

* * * * *